United States Patent [19]

Magistro

[11] Patent Number: 4,937,637
[45] Date of Patent: Jun. 26, 1990

[54] DUAL READING HEAD TRANSMISSION/REFLECTION DENSITOMETER

[75] Inventor: Anthony J. Magistro, Newburgh, N.Y.

[73] Assignee: Kollmorgen Corporation, Simsbury, Conn.

[21] Appl. No.: 309,096

[22] Filed: Feb. 10, 1989

[51] Int. Cl.$^5$ ................ G01N 21/47; G01N 21/59
[52] U.S. Cl. ............................................ 356/73
[58] Field of Search .................... 356/73, 443, 446; 250/227

[56] References Cited

U.S. PATENT DOCUMENTS

| | | | |
|---|---|---|---|
| 3,102,202 | 8/1963 | Sweet | 356/443 |
| 3,542,479 | 11/1970 | Sibalis | 356/231 |
| 3,746,869 | 7/1973 | Lindstedt et al. | 356/73 |
| 3,998,551 | 12/1976 | Suga | 356/73 |
| 4,171,909 | 10/1979 | Kramer et al. | 356/73 |
| 4,281,932 | 4/1981 | Young | 356/416 |
| 4,352,988 | 10/1982 | Ishida | 356/435 |
| 4,473,298 | 9/1984 | Sakamoto | 356/432 |
| 4,564,290 | 1/1986 | Bell et al. | 356/73 |
| 4,645,351 | 2/1987 | Seto | 356/443 |
| 4,669,885 | 6/1987 | Ina | 356/443 |

OTHER PUBLICATIONS

Macbeth sale brochures: (1) Graphic Arts Densitometer Selection Guide; (2) A Full Range of Prepress Densitometers; (3) Densitometers for Color Prepress Applications; (4) Densitometers for Black and White Prepress Applications; (5) Densitometers for the Modern Pressroom; (6) Full Function Bench Top Densitometers for the Pressroom; (7) Dual and Single Function Bench Top Densitometers for the Pressroom; (8) Color Checker Portable Pressroom Densitometers with Auto Function Select; (9) Color Checker Auto Density Dot and Auto Density Portable Pressroom Densitometers; (10) Macbeth Products for the Protographic Industry; (11) Macbeth Densitometers for Microfilm; (12) Macbeth TD 932 Transmission Densitometer for X-ray.

Primary Examiner—Vincent P. McGraw
Attorney, Agent, or Firm—Morgan & Finnegan

[57] ABSTRACT

A dual reading head transmission/reflection densitometer is disclosed which offers superior performance and reduced manufacturing costs. The invention employs two separate measuring heads, each containing their own collection optical system mounted in a single swing arm. Reflected or transmitted light is transmitted from the appropriate collection head through fiber optic leads to a bifurcated fiber bundle and then to the photodetector assembly.

20 Claims, 2 Drawing Sheets

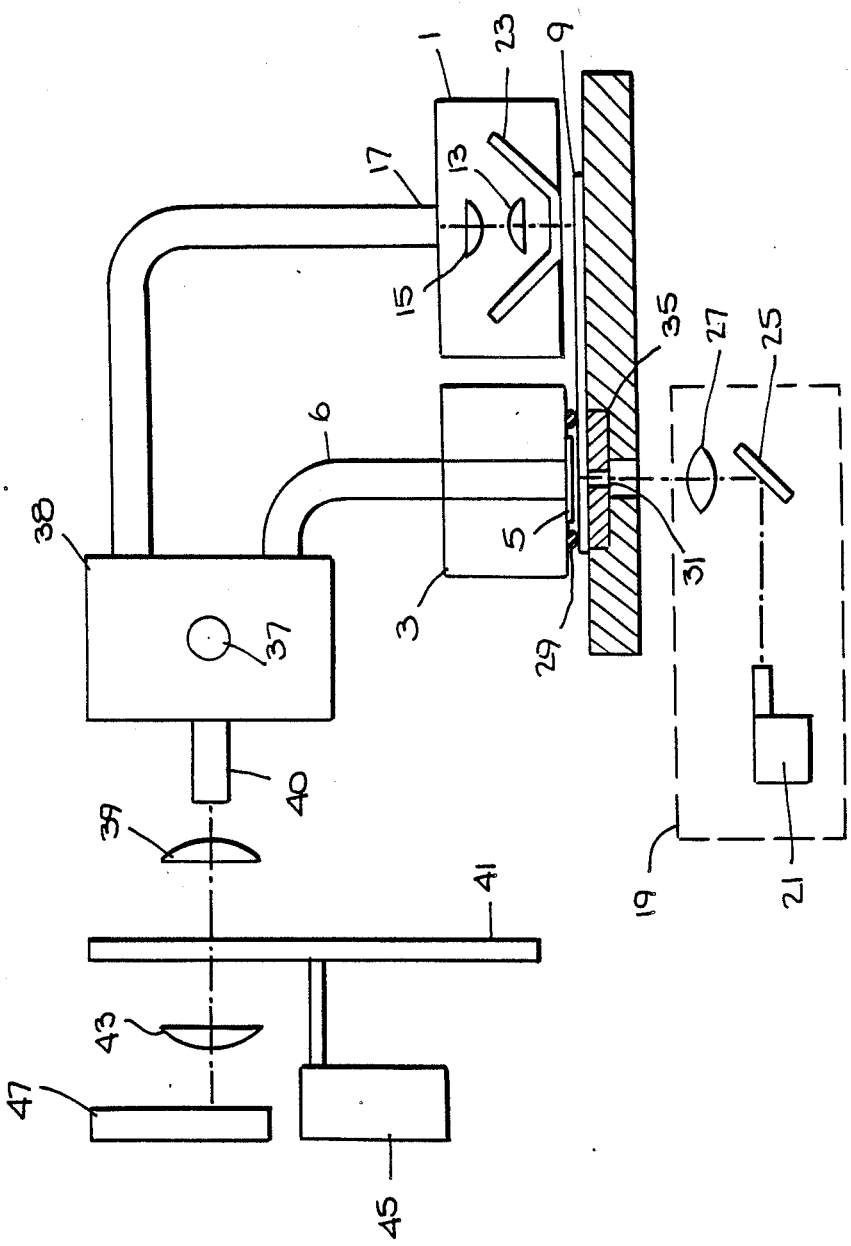

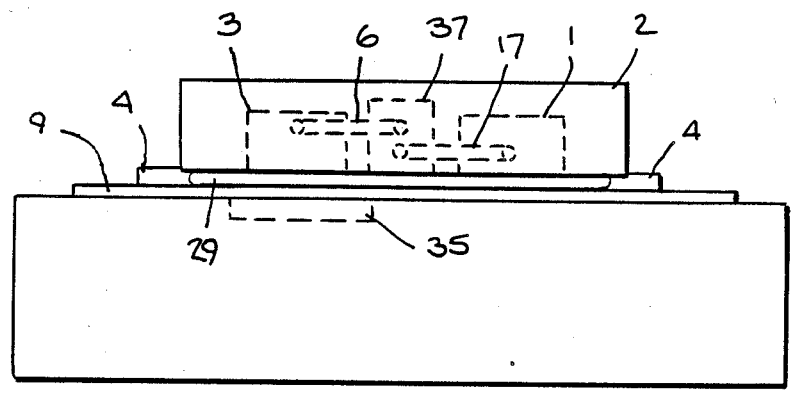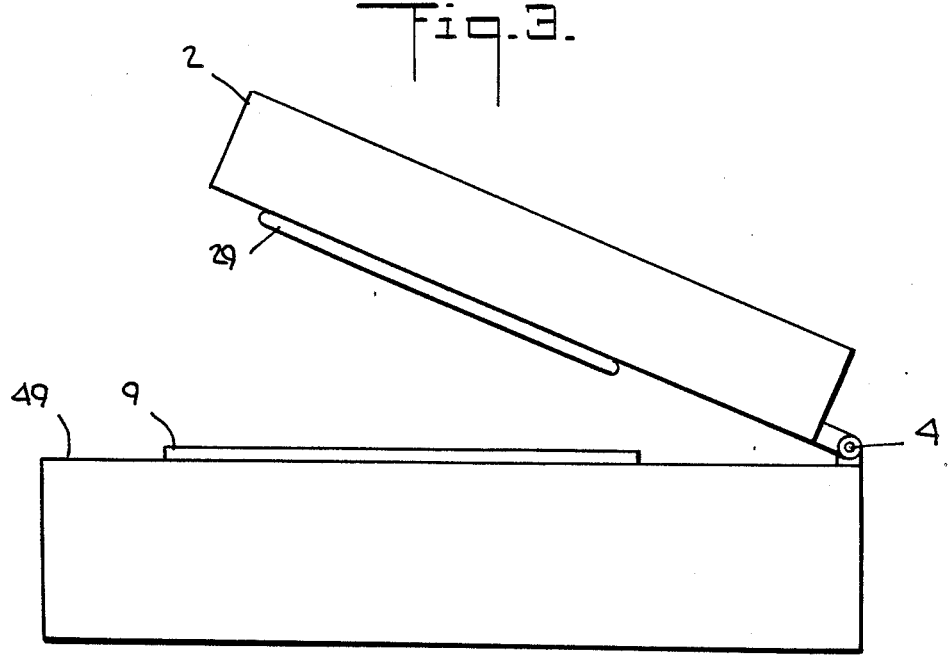

DUAL READING HEAD TRANSMISSION/REFLECTION DENSITOMETER

BACKGROUND AND OBJECTS OF THE INVENTION

1. Field of the Invention

The present invention relates generally to optical densitometers and more particularly, to an improved densitometer which can measure either a sample's reflectance factor or transmittance factor with equally high accuracy.

2. Description of the Prior Art

It is important, when evaluating the optical properties of a material, to reliably and accurately ascertain its reflectance factor and/or transmittance factor. The reflectance factor, R, is a measure of the amount of light which is reflected from a sample's surface. It is defined as the ratio of measured reflected flux from the specimen to the measured reflected flux from a perfect-reflecting, perfect diffusing material located in place of the sample. Standards for measuring reflectivity are set out in ANSI/ISO 5/4-1983, ANSI PH2.17-1985. The transmittance factor is a measure of how much light can pass through a sample. It is defined as the ratio of the measured flux transmitted by the specimen to the measured flux when the specimen is removed from the sampling aperture. Standards for measuring the transmittance factor are established in ANSI/ISO 5/2-1985, ANSI PH2.19-1986.

In practice, the reflectance factor is measured by shining light onto the sample's surface at an angle of approximately 45° and measuring the intensity of light reflected perpendicularly to the surface (ANSI standards specify the exact geometry). To measure the transmittance factor light is shined perpendicularly onto one side of a sample and the intensity of light passing directly through it is measured (again, ANSI standards specify the exact geometry).

Although it is relatively simple to construct an instrument which precisely measures only one of these values, it is more difficult to build one capable of accurately measuring both the reflectance and transmittance factors. Higher intensity light is needed to measure the transmittance factor than the reflectance factor. However, it may be difficult to find a light source which performs optimally at both these high and low light levels. In practice some densitometers use a plurality of light sources, as does U.S. Pat. No. 3,102,202, issued to Sweet, although other combination detectors employ a single light source, such as that disclosed in U.S. Pat. No. 3,542,479, issued to Sibalis. Neither of these solutions is entirely satisfactory, however, because both designs have features which compromise measuring precision.

Applicant's invention avoids the limitations of both the single and multiple lamp densitometers and as a result it offers superior performance. Multiple lamp units such as Sweet's usually include complicated optical paths which guide the reflected or transmitted light to the detector. Depending on which lamp is illuminated either reflected or transmitted light will be directed to the detector. Although the use of two lamps allows both to be selected to provide optimal lighting for each technique, the complexity of the multiple optical paths necessary to transmit the light to the detector means these densitometers cannot be built to perform optimally for both techniques. In fact, these "combined" devices will be less accurate than separate "dedicated" densitometers able to measure only the reflectance factor or transmittance factor.

As already noted, the design of single lamp densitometers able to measure transmittance and reflectance optical properties involves similar compromises which cause measuring inaccuracies. A single lamp may not emit light having the proper frequency distribution for differing intensities, and this reduces measuring accuracy. Single lamp densitometers also usually have several light detectors. Although the light paths are simplified, the costs are increased by the additional circuitry. Instrument calibration also becomes more complicated. See, for example, U.S. Pat. No. 4,352,988 to Ishida.

OBJECTS OF THE INVENTION

It is therefore an object of the present invention to provide a relatively simple and inexpensive densitometer which can accurately measure both the reflectance factor and transmittance factors of a sample.

Another object of the present invention is to provide a densitometer which does not possess the inherent measuring imprecision found in densitometers which employ "compromise" optics.

Another object of the present invention is to provide a densitometer which possesses the advantages of both dual lamp and single lamp densitometers while avoiding the shortcomings of each.

Yet another object of this invention is to provide a densitometer which is compact yet accurate.

Objects and advantages of the invention are set forth in part herein and in part will be obvious herefrom, or may be and attained by means of the instrumentalities and combinations pointed out in the appended claims.

The invention consists in the novel parts, constructions, arrangements, combinations, steps and improvements herein shown and described.

It will be understood that the foregoing general description and the following detailed description as well are exemplary and explanatory of the invention but are not restrictive thereof.

The accompanying drawings, referred to herein and constituting a part hereof, illustrate preferred embodiments of the invention, and together with the description, serve to explain the principles of the invention.

SUMMARY OF THE INVENTION

Heretofore, no single densitometer has been available which successfully avoids the shortcomings of both single and double lamp devices.

In accordance with the invention, Applicant provides a dual head densitometer which offers the advantages of the combined reflectance, transmittance type of devices while not suffering their problems and drawbacks.

Most importantly, Applicant's invention does not suffer from the optical performance compromises usually required to obtain a combined reflectance/transmittance densitometer.

Applicant achieves this remarkable result by employing two separate measurement heads, one having the appropriate illumination and collection measuring optics for reflectance operation, the other transmittance, and a single photodetector assembly which services both of these heads. Fiber-optic light guides transmit the light from the measurement heads to the photodetector. The two fiber-optic light guides connect at a fiber-optic junction which leads to the photodetector.

The user measures the desired optical property by selecting which lamp is energized, and the device is suitably constructed to minimize the amount of light "leaking" through the non-energized measurement head. Advantageously, low cost fiber-optics eliminate the need for mirrors and prisms to guide the light to the photodetector, thereby reducing the cost and size of the device. The use of fiber optics also eliminates the need to maintain a series of lenses, mirrors, prisms, detector, etc., in close alignment. As a further advantage of the invention, the use of a fiber-optic junction permits the use of a single detector, thereby further reducing the cost of the device.

These and other objects and advantages are accomplished in a relatively low cost, compact unit which provides precise and accurate transmittance and reflectance measurements without compromise.

BRIEF DESCRIPTION OF THE DRAWINGS

The accompanying drawings, referred to herein and constituting a part hereof, illustrate the preferred embodiments of the product of the present invention, and together with the description serve to explain the principles of the invention, in which:

FIG. 1 is a schematic view of the optical and mechanical components of the combined reflectance/transmittance densitometer in accordance with the present invention;

FIG. 2 is a front elevation view of the densitometer in accordance with the present invention, illustrating both measurement heads disposed in one measurement arm;

FIG. 3 is a side elevation view of the densitometer in accordance with the invention.

DESCRIPTION OF THE PREFERRED EMBODIMENT

Referring now to FIGS. 1–3 of the accompanying drawings, there is illustrated a preferred embodiment of a dual reading head densitometer constructed in accordance with the present invention. As preferably embodied herein, the device is advantageously adapted for precisely measuring the reflectance and transmittance factors of photographic materials.

Turning now to FIG. 1, a dual head densitometer according to the present invention is shown in schematic form, with boxes 1 and 3 corresponding to and designating the reflective and transmissive collection heads, respectively. Preferably, both collection heads are commonly mounted in a hinged arm 2 which rotates about a hinge 4 to bring both collection heads into contact with a sample 9 placed onto the sampling stage (See FIGS. 2 and 3). Referring again to FIG. 1, reflective measuring head 1 contains an approximately annular illuminator 23 which shines light of suitable frequency and intensity onto sample 9 at approximately a 45° angle. In accordance with ANSI/ISO 5/4-1983, ANSI PH2.17-1985 the reflectance factor of the sample is based upon the intensity of the light reflected perpendicularly to the surface plane of the sample. Light reflected perpendicularly from sample 9 passes through a stray light stop 11, a collection lens 13 and an imaging lens 15, all located in the reflective measuring head 1. The light emerging from imaging lens 15 is collimated, and enters a reflectance fiber-optic lead 17.

The reflectance measuring head 1 is positioned so that when the hinged arm is lowered it isolates the sample, preventing ambient light from entering the reflective optics and causing an erroneous measurement.

Transmissive measuring head 3 is positioned directly above an illuminating subassembly 19. The illuminating subassembly 19 contains an illuminating lamp 21 which emits light of suitable frequency and intensity. Light from lamp 21 is reflected by a cold mirror 25 through an illuminator lens 27 and a transmission aperture 31 onto a transmission portion of sample 9. The lamps used in transmission densitometers must emit high intensity light and they unavoidably produce a great deal of infrared light which undesirably heats the sample. In the present invention, infrared heating of the sample is minimized by placing a cold mirror in the light path. The cold mirror reflects desired visible light toward the sample but transmits the infrared radiation that would cause sample heating. Illuminator lens 27 focuses the light coming from the lamp and increases its intensity. In the preferred embodiment as depicted provisions are made to vary the transmission aperture 31, such as by providing a removable aperture plate 35 which fits into a socket in the base. An assortment of plates having different sized apertures allows the user to choose the proper size light beam in accordance with ANSI/ISO 5/2-1985, ANSI PH2.19-1986.

Light from the illuminating subassembly 19 passes through aperture 31 to reach the sample 9 placed on the measurement table. Light transmitted through the sample 9 passes through a pot opal diffuser 5 mounted in the measuring head 3 and enters the transmittance fiber-optic lead 6.

Transmittance reflectance head 3 is also provided with a compressible O-ring 29 surrounding pot opal 5 and the area of the sample to be measured. Both O-ring 29 and pot opal 5 are attached to the lower surface of transmissive measuring head 3. Pot opal diffuser 5 is slightly smaller and thinner than the O-ring 29 and it is disposed within the O-ring 29. Thus, when transmission measuring head 3 is lowered onto sample 9 O-ring 29 seals against the sample 9 and compresses slightly, allowing pot opal diffuser 5 to also contact sample 9. This arrangement helps prevent ambient environmental light from erroneously increasing the measured transmitted flux. Light leaving transmission aperture 31 passes through the sample 9 and pot opal diffuser 5 and enters fiber optic lead 6.

Fiber-optic leads 6 and 17 are joined by a fiber-optic coupling 37, such as a combined fiber optic coupling, thereby constituting a bifurcated fiber bundle 38. Light entering either fiber-optic lead 6 or 17 passes through the fiber-optic coupling 37 in the bifurcated fiber bundle 38 and emerges through common fiber 40. Light transmitted by common fiber 40 is collimated by a detector collection lens 39 and condensed by a detector imaging lens 43 onto a photodetector 47, which measures the light intensity. In the preferred embodiment of the invention a filter wheel 41 is interposed between the collection and imaging lenses 39 and 41, respectively. Filter wheel 41 contains 3 status "A", 3 status "M" and one "visual" (photopic) filters all in accordance with ANSI standard PH2.18-1984. The "visual" filter is used when measuring neutral (black and white) tones. The filter wheel 41 is rotated by a stepping motor 45 to place the appropriate filter (not shown) in the light's path. The stepping motor is operated by conventional control means, in themselves well-known.

In accordance with the preferred embodiment of the present invention, reflective measuring head 1 and transmissive reflecting head 3 are both commonly mounted alongside one another in a hinged arm 2 (see FIG. 2). Hinged arm 2 pivots about hinge 4 to rotate toward and away from the sampling stage. To use the invention hinged arm 2 is raised so that the sample 9 being measured can be placed between support 49 and the appropriate measurement head. The swing arm 2 is lowered and the densitometer operated in either the reflectance or transmittance mode to measure the desired properties. Advantageously, both reflectance and transmittance measurements may be taken on the same sample 9 by moving the sample 9 slightly and changing modes.

To use the invention to measure either reflectance or transmittance factor the user simply illuminates the appropriate lamp, as by operating a mode selection switch (not shown). The device is constructed to prevent measuring inaccuracies caused by stray light entering the non-energized head and passing through the fiber-optic lead to the photodetector. Those of ordinary skill in the art will recognize that light-blocking means such as shutters or shrouds can be employed to further reduce any residual effects of stray light.

The invention in its broader aspects is not limited to the specific embodiments herein shown and described but departures may be made therefrom within the scope of the accompanying claims, without departing from the principles of the invention and without sacrificing its chief advantages.

By way of example and not limitation, it is contemplated that each measuring head could be mounted in an independently movable swing arm, with the appropriate arm being used in each mode.

I claim:

1. A dual reading head transmission/reflection densitometer comprising:
   a sample stage having a transmission measurement zone and a reflection measurement zone;
   transmission illumination means for illuminating said transmission measurement zone;
   reflection illumination means for illuminating said reflection measurement zone;
   transmission collection optics for collecting light from said transmission illumination means transmitted through a transmission sample disposed at said transmission measurement zone;
   reflection collection optics for collecting light from said reflection illumination means reflected by a reflection sample disposed at said reflection zone;
   a first optical fiber for receiving light from said transmission collection optics;
   a second optical fiber for receiving light from said reflection collection optics;
   optical coupling means for combining the output of said first and second optical fibers and transmitting a combined light beam;
   detector means for receiving and measuring the intensity of said combined light beam; and
   mode switching means for selecting, in the alternative, between transmission mode or reflection mode of operation.

2. The dual reading head transmission/reflection densitometer as in claim 1, wherein said transmission collection optics further comprise a pot opal diffuser disposed so that light transmitted by the sample passes through said pot opal diffuser before entering said first optical fiber.

3. The dual reading head transmission/reflection densitometer as in claim 1 wherein said transmission illumination means and said transmission collection optics are constructed in accordance with ANSI standard ANSI/ISO 5/2-1985, ANSI PH2.19-1986.

4. The dual reading head transmission/reflection densitometer as in claim 1, wherein the reflection illumination means further comprise an annular illuminator configured and dimensioned to illuminate a sample point at an incident angle of approximately 45°.

5. The dual reading head transmission/reflection densitometer as in claim 4, wherein the reflection illumination means and the reflection collection optics are constructed in accordance with ANSI standard ANSI/ISO 5/4-1983, ANSI PH2.17-1985.

6. The dual reading head transmission/reflection densitometer as in claim 4, wherein the reflection collection optics further comprise:
   a stray light stop;
   a collection lens;
   an imaging lens; and
   the stray light stop, collection lens and imaging lens are all disposed about an axis so that light reflected perpendicularly from the illuminated sample point passes through the stray light stop, collection lens and imaging lens and enters said second fiber-optic lead.

7. The dual reading head transmission/reflection densitometer as in claim 1, wherein said optical coupling means further comprise a combined fiber-optic coupling.

8. The dual reading head transmission/reflection densitometer as in claim 1 wherein said detector means further comprises:
   a detector collection lens;
   a detector imaging lens; and
   a detector,
   said detector collection lens receiving said combined light beam and transmitting said combined light beam to said detector imaging lens, said detector imaging lens focusing said combined light beam onto said detector.

9. The dual reading head transmission/reflection densitometer as in claim 8 wherein the detector means further comprise:
   a rotatable filter wheel having a plurality of filters, said rotating filter wheel being disposed is the optical path of said combined light beam between said detector collection lens and said detector imaging lens; and
   means for rotating said filter wheel.

10. A dual reading head transmission/reflection densitometer as in claim 9 wherein the filter wheel further comprises a plurality of filters in accordance with ANSI standard PH2.18-1984.

11. The dual reading head transmission/reflection densitometer as in claim 9 wherein said detector collection lens collimates said combined light beam.

12. A dual reading head transmission/reflection densitometer as in claim 1 wherein said mode switching means operates to activate one illumination means while disconnecting the other illumination means.

13. A dual reading head transmission/reflection densitometer as in claim 12 further comprising light shroud means for reducing the amount of ambient light entering the collection optics associated with the disconnected illumination means.

14. A dual reading head transmission/reflection densitometer comprising:

a sample stage having a depression in its upper surface;
a transmissive measuring head;
a reflective measuring head;
an optical coupling means having first and second optical inputs and a single output;
a first optical fiber lead connected to said transmissive measuring head and said first optical input of said optical coupling means;
a second optical fiber lead connected to said reflective measuring head and said second optical input of said optical coupling means;
transmissive beam dimensioning means;
transmissive illuminating means disposed beneath said depression for directing a transmissive illumination beam through said transmissive beam dimensioning means toward said transmissive measuring head;
reflective illumination means for directing a reflective illumination beam toward said sample stage adjacent said reflective measuring head;
a detector assembly optically connected to the output of said optical coupling means; and
mode selection means for selecting transmissive or reflective mode of operation.

15. The dual reading head transmission/reflection densitometer as in claim 14 wherein said transmissive measuring head further comprises:
a head shell having a lower surface, which has an opening;
a pot opal diffuser attached to said lower surface over said opening;
an O-ring joined to the lower surface, the O-ring being larger than the pot opal; and
said first optical fiber lead being positioned in the head shell so that light passing through said pot opal diffuser and said opening enters said first optical fiber.

16. The dual reading head transmission/reflection densitometer as in claim 14 wherein said transmissive illuminating means further comprise:
a transmissive illuminating lamp;
a transmissive illuminator lens; and,
a cold mirror;
said cold mirror reflecting light from said transmissive illuminating lamp to said transmissive illuminator lens, said transmissive illuminator lens focusing said light through said transmissive beam dimensioning means.

17. The dual reading head transmission/reflection densitometer as in claim 16 wherein said transmissive beam dimensioning means further comprise a plate having an aperture, said plate being configured and dimensioned to fit securely yet removably in said sample stage depression.

18. The dual reading head transmission/reflection densitometer as in claim 17 wherein the reflective measuring head further comprises:
an annular illuminator configured and dimensioned to illuminate a point on said sample stage at an incident angle of approximately 45°;
a stray light stop;
a reflective collection lens; and
a reflective imaging lens;
said stray light stop, collection lens and imaging lens being disposed about an optical axis so that light reflected perpendicularly to said sample stage passes through said stray light stop, collection lens and imaging lens and enters said second fiber-optic lead.

19. The dual reading head transmission/reflection densitometer as in claim 18 wherein said transmissive measuring head and said reflective measuring head are disposed in a swing arm pivotally mounted to a base supporting said sample stage, such that said reflective measuring head and said transmissive measuring head can be rotated toward or away from said sample stage.

20. The dual reading head transmission/reflection densitometer as in claim 19 wherein said detector assembly further comprises:
a detector collection lens;
a detector imaging lens;
a rotatable filter wheel having a plurality of filters;
means for selectively rotating the filter wheel; and
a photodetector;
said detector collection lens receiving and collimating said single output from said optical coupling means and transmitting said collimated single output through said filter wheel to said detector imaging lens, said detector imaging lens focusing said collimated, filtered beam onto said photodetector.

* * * * *